United States Patent [19]

Choi

[11] 4,318,302
[45] Mar. 9, 1982

[54] METHOD OF DETERMINING MINE ROOF STABILITY

[75] Inventor: Dai-Shik Choi, Ponca City, Okla.

[73] Assignee: Conoco Inc., Ponca City, Okla.

[21] Appl. No.: 969,079

[22] Filed: Dec. 13, 1978

[51] Int. Cl.³ .............................................. F16B 31/02
[52] U.S. Cl. ........................................ 73/761; 73/579
[58] Field of Search ................ 73/582, 594, 761, 784, 73/581, 579

[56] References Cited

U.S. PATENT DOCUMENTS 2,549,076 4/1951 Gallagher et al. ..................... 73/594
4,150,576 4/1979 Tarpley, Jr. .......................... 73/594

FOREIGN PATENT DOCUMENTS 238209 2/1969 U.S.S.R. ............................... 73/581

Primary Examiner—Jerry W. Myracle
Attorney, Agent, or Firm—William J. Miller

[57] ABSTRACT

A method and apparatus for determining the tension of mine roof bolts and/or mine roof stability which utilizes the natural vibration frequency of the seated roof bolt and/or roof structure to provide indication of bolt tension and/or roof stability.

1 Claim, 5 Drawing Figures

METHOD OF DETERMINING MINE ROOF STABILITY

CROSS-REFERENCE TO RELATED APPLICATIONS

The present application is related to a co-pending application entitled "Electronic Mine Roof Testing Apparatus", now U.S. Pat. No. 4,281,547 Ser. No. 37,691, filed May 10, 1979, as assigned to the present assignee.

BACKGROUND OF THE INVENTION

1. Field of the Invention

The invention relates generally to mine roof testing methods and apparatus and, more particularly, but not by way of limitation, it relates to improved testing apparatus for determining mine roof bolt tension as well as general mine roof stability.

2. Description of the Prior Art

The prior art has seen numerous types of tensometers and similar devices for making some determination as to the secure positioning and rigidity of a metallic object. Prior art patents which are particularly related to testing of a metal bolt or the like have primarily relied upon ultrasonic energy behavior in deriving parameter indicators illustrating rigidity or reliability. U.S. Pat. No. 3,307,393 in the name of Kessler teaches a stress measuring device wherein determination is made by measuring a change in electrical impedance due to an increase in length of the fastener. This method provided a marked degree of improvement over the prior methods of simply measuring the degree of torque as applied to the fastener in seating it to operative position. U.S. Pat. No. 3,306,100 in the name of Wilhelm et al. discloses yet another form of ultrasonic bolt tension tester which utilizes as an indicator, frequency as a function of the length of the fastener, Young's modulus of elasticity and the density of the fastener; however, there is no direct relationship as to the tension of the fastener contributing to the final readout. The method measures the changes in length and then interprets increased length to increased tension of the fastener.

U.S. Pat. No. 3,759,090 in the name of McFaul et al. provides yet another and more recent ultrasonic tensometer wherein the method serves to measure the elongation of a bolt due to tension and thereafter extrapolates the magnitude of tension. Finally, a recently issued U.S. Pat. No. 4,062,229 as issued on Dec. 13, 1977 makes disclosure of a method similar to that set forth and claimed in the present application.

SUMMARY OF THE INVENTION

The present invention contemplates a method and apparatus for accurately determining mine roof bolt tension and for determining mine roof stability in general. The present method, as regards roof bolt stability, may be applied to either anchor bolts or grouted roof bolts to provide output bolt tension indication, and the method and apparatus provides for a further feature of permanently installed test equipment responsive to operation from a remote location whereby wide-area mine roof indication can be read rapidly and accurately. The method consists of striking a roof bolt or mine roof position to effect generation of sound at the natural frequency and, thereafter, to spectrum analyze transduced pickup of the natural frequency sonic energy thereafter to provide readout indicating the bolt tension or roof position stability.

Therefore, it is an object of the present invention to provide a method for rapidly and accurately indicating mine roof bolt tension.

It is also an object of the invention to provide a method for rapidly and accurately providing readout of stability at a selected mine roof position.

It is still further an object of the present invention to provide a system utilizing the method of the invention wherein a large expanse of mine roof or a large plurality of mine roof bolts can be automatically tested by interrogation from a remote location with attendant readout provided.

Finally, it is an object of the present invention to provide an improved method and apparatus enabling a tangible safety factor in and around underground mine structures.

Other objects and advantages of the invention will be evident from the following detailed description when read in conjunction with the accompanying drawings which illustrate the invention.

BRIEF DESCRIPTION OF THE DRAWINGS

FIG. 5 is a block diagram of a mine tunnel system for providing large area roof stability indication.

DETAILED DESCRIPTION OF THE INVENTION

The present method and apparatus utilizes the natural vibrating frequency of a rock bolt or mine roof position to measure bolt tension or roof stability, respectively. The supporting mechanism of rock bolts is believed to originate from tension applied to them and the degree of performance is determined by their ability to sustain this tension. Therefore, early detection of improper tension in rock bolts is necessary in order that they may be tightened adequately and in sufficient time to avoid weakened roof situations. In present practice, a torque wrench is generally used to determine the bolt tension. This method leads to erroneous values when the bolt is rusty and/or installed improperly. For example, a slight misalignment of a head nut, washer and a bearing plate may increase the torque required to tighten the bolt, but will impart no further tension to the bolt shaft itself; thus, and according to U.S. Bureau of Mines publications, bolt tensions determined with a torque wrench may have as much as 35% error.

Figure 1:
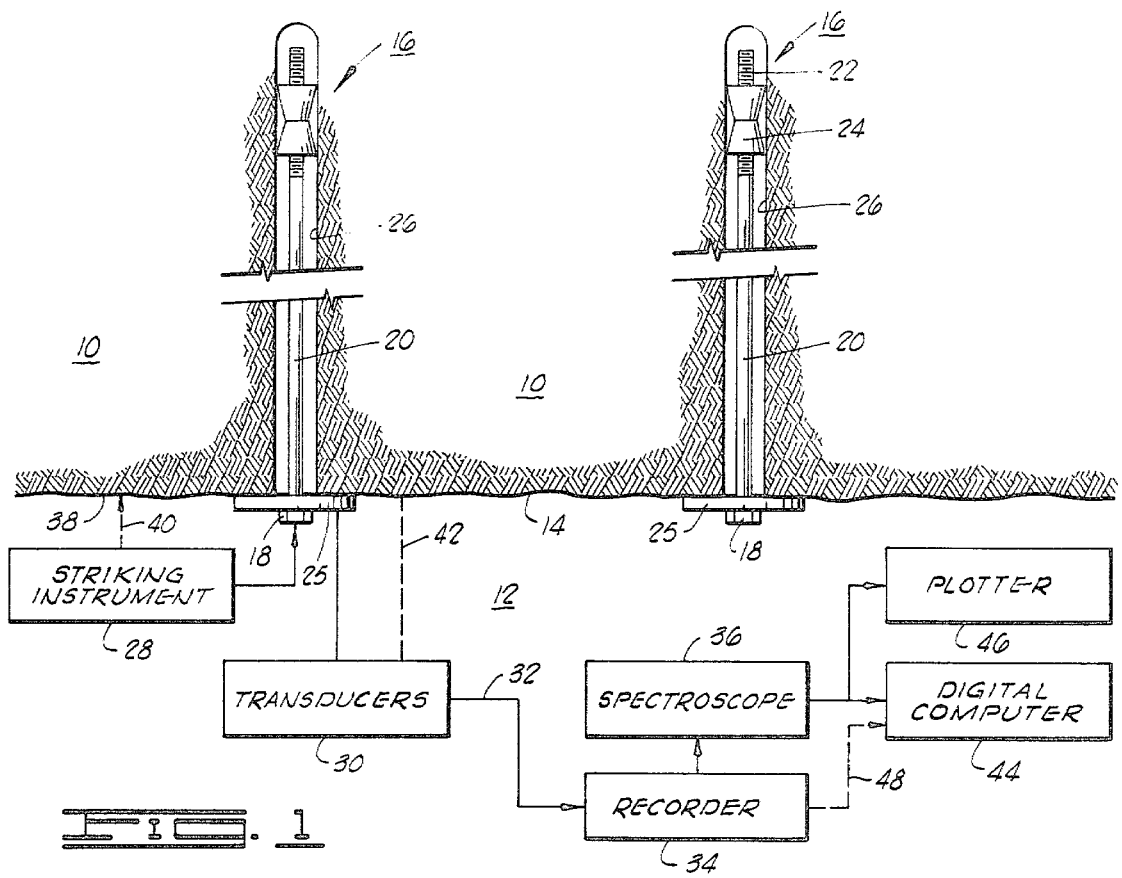
FIG. 1 is an idealized showing of a portion of mine roof section with testing apparatus shown in block diagram.

Utilizing equipmentation as shown generally in FIG. 1, the present invention measures rock bolt tension or mine roof stability by recording and analyzing sound waves generated by the bolt or roof portion itself when that subject is excited by some source. The method differs from the prior art in that (1) it does not require a positive coupling to the bolt; (2) it determines absolute bolt tension at any time rather than relative bolt tension as is measured with prior used strain gauges or compression pads; and (3) it measures directly the level of bolt tension, not the level of bolt torque.

Referring to FIG. 1, a rock portion or mine roof 10 over a mine tunnel 12 delineates a roof surface 14 which is maintained stable during the various mining operations by means of pluralities of strategically placed roof bolts 16. In this case, roof bolts 16 are of the expanding anchor type, but it should be understood that grouted bolts will sometimes be used and these are subject to the same determinations as to stability and tension measurement.

The roof bolt 16 may be a number of feet in length and it consists of a bolt head 18 as rigidly formed with a bolt shaft 20 having threaded end 22 for fastened engagement within a threaded anchor nut 24. The roof bolt 16 is then inserted through a bearing plate 25 and up within a pre-drilled hole 26 whereupon it is tightened at bolt head 18 to the requisite torque or rigid seating indicated by such torque. Oftentimes the alternative to the anchor fastener roof bolt is utilized and this consists of a well-known form of elongated bolt and shaft that is seated up within a pre-drilled bore and rigidly retained therein by means of grouting with selected ones of polyester resins. In either case, it is their function to maintain vertical alignment of the roof or ceiling strata of shale-like rock layers thereby to prevent sideways slipping or shifting, a primary contributor to tunnel roof weaknesses.

In basic form, the roof bolt test can be made by striking the bolt head 18 with a striking instrument 28, e.g., the geologic hammer, and thereafter detecting and recording the natural vibrations by means of one or more transducers 30 providing output 32 to a recorder 34 for selective playback to a spectroscope 36. Alternatively the roof bolt test can be made by normal tightening of the roof bolt head 18, which tightening will excite the roof bolt, developing natural vibration which can be detected by one or more transducers 30. Application of striking instrument 28 to roof portion 38, as shown by dash-line 40, will provide the same natural vibrations for the roof portion 38 such that transducers 30 may detect such vibrations as connected via dash-line 42 thereby to provide the similar output to recorder 34 and spectroscope 36.

Output from the spectroscope 36 may then be applied to a suitable form of digital computer 44, e.g., one of the commercially available forms of mini-computer or the now available specially programmed microprocessor circuits, and the output from spectroscope 36 is further applied to a plotter 46 of well-known type. In addition, output from the recorder 34 may be applied, as shown by dashed line 48 to digital computer 44 thereby to provide still further versatility as to signal enhancement and output presentation.

The transducers 30, when contacting either a bearing plate 25 or a mine roof portion as at dash line 42, may be any of the conventional form of seismic probe responsive to vertical motion and having a response range in the order of 10–10,000 HZ., or transducers 30 may be microphones such as the Model 575S available from Shure Company having a frequency response range of 40–15,000 Hz. Also, conventional accelerometers may be used. When using either type of transducer 30 it is desirable to orient selected ones both vertically and horizontally to best pick up both vertical and horizontal axes of vibration, as will be further described below. The recorder 34 may be any suitable audio recorder, preferably a multi-channel audio frequency recorder thereby to receive input from a multiple of seismic probes and/or microphone transducers. Selected outputs from recorder 34 are then spectrum analyzed in spectroscope 36, e.g., a Model SD330A REAL TIME ANALYZER as is available from Spectral Dynamics Corporation of San Diego, Calif. Thereafter, the analyzed output from spectroscope 36 may be graphically indicated in a plotter 46, such as an Omniographic 2000, that provides a plotted output indicator of the type shown in FIG. 2 to be further described below.

In the measuring of roof bolt tension, the roof bolt is excited or struck at bolt head 18 thereby to vibrate transversely in a plane with respect to the straight bolt axis. Thereafter, the possible deflection modes of a bolt of particular length L can be determined in accordance with the following differential equation:

$$\frac{\partial^2}{\partial x^2}\left(EI\frac{\partial^2 W}{\partial x^2}\right) - \frac{\partial}{\partial x}\left(S\frac{\partial W}{\partial x}\right) + \rho\frac{\partial^2 W}{\partial t^2} = 0 \quad (1)$$

Where
$W(x,t)$ is the deflection of the bolt
$x$ is the distance measured along the bolt axis
$S$ is tension of the bolt
$E$ is Young's modulus of the material of the bolt
$I$ is the moment of inertia of the bolt mid-cross section, and
$\rho$ is the linear mass density of the bolt.

In order to calculate the modes of natural fequency, it may be assumed that the possible deformation is as follows:

$$W(x,t) = Y(x)\sin(\omega_n t + \phi) \quad (2)$$

where $\omega_n$ is natural circular frequency. Then the equation (1) can be reduced to an ordinary differential equation of the form:

$$EI(d^4Y/dx^4) - S(d^2Y/dx^2) - \rho\omega_n^2 Y = 0 \quad (3)$$

The solution of the equation (3) may then be assumed to be:

$$Y = C_1\sin(\lambda_1 x + \phi_1) + C_2\sin(\lambda_2 x + \phi_2) \quad (4)$$

Where $\lambda_1$ and $\lambda_2$ are the solution of the frequency equation:

$$EI\lambda^4 + S\lambda^2 - \rho\omega_n^2 = 0 \quad (5)$$

Assuming that both ends of the bolt are clamped, then it can be shown that $\phi_1$, $C_2$ and $\phi_2$ become zero. Consequently, $\lambda_1$ can be rewritten as $$\lambda = n\pi/L \quad (6)$$

Where n is a positive integer. Then, with combination of the equation (5) and (6) and subsequent rewriting, we derive the following equation:

$$\omega_n^2 = \frac{1}{4EI\rho}\left[\left(\frac{2EI\pi^2 n^2}{L^2} + S\right)^2 - S^2\right] \quad (7)$$

This equation may be used to calculate the vibrating frequency for various lengths of a particular width diameter roof bolt in which bolt tension and frequency are expressed in the unit of pound and Hz., respectively. The roof bolt at whatever tension will vibrate various modes of natural frequency when excited, and while mode amplitudes will vary somewhat there is still a uniform indicator as to actual bolt tension.

Figure 2:
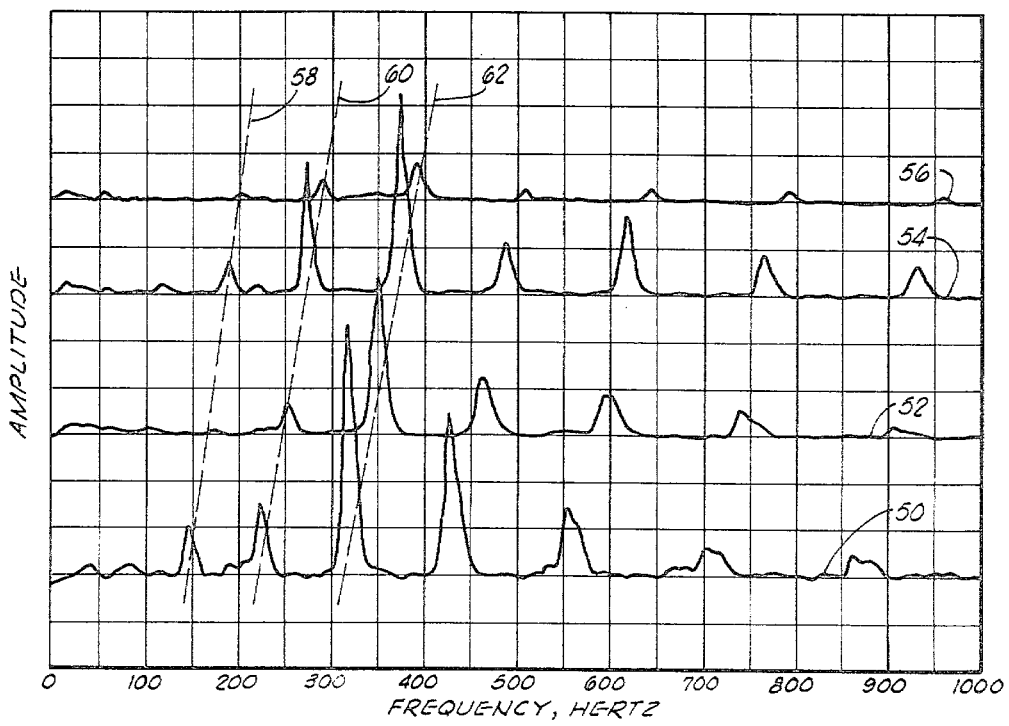
FIG. 2 is a graph for a plurality of strike signals as illustrated in amplitude versus frequency.

Referring to FIG. 2, there is indicated a graph relating to a particular roof bolt in situ, the particular bolt being five feet long and ⅜ inch in diameter, and it was tensioned by use of a torque wrench in conventional manner. The bolt was then excited to vibrate by means of a geologic hammer and the bolt vibrations were detected by a microphone for subsequent recording on magnetic tape.

FIG. 2 illustrates the relative amplitudes versus frequency in Hz. for a five inch diameter roof bolt, five feet in length, (1) when excited at a torque of 40 foot-pounds as at curve 50, (2) when excited at 80 foot-pounds as at curve 52, (3) when excited at 140 foot-pounds as at curve 54, and (4) when excited at 170 foot-pounds as at curve 56. As can be readily noted, there are a series of distinct vibrational modes that move to progressively higher frequency for progressively greater tensions. Also, it can be noted that the mode amplitude responses are significantly greater when the roof bolt is subjected to the lesser tension. Thus, since the bolt with lower tension vibrates with bigger amplitude at a given energy input, such bolts with lower tension are easier detected in accordance with the present method.

While eight distinct modes of natural frequency vibration are illustrated for each of curves 50–56, it is readily apparent that modes 3, 4 and 5, i.e., mode alignments 58, 60 and 62, will offer the most readable indications. In particular, the mode for alignment 62 offers the clearest indication and an optimum lineup for frequency versus amplitude comparison relative to the four distinctly different tensions of roof bolt as indicated on respective curves 50–56. Discrepancies are slight and such variation is due to the fact that the roof bolt is supported by the bearing plate 24 acting as an elastic spring when subjected to dynamic loading conditions. Such variation is analytically predictable and is accounted for in conventional manner in data computation and final output plot.

To further verify the natural frequency of a roof bolt, a table has been compiled for a bolt having characteristics of a bolt length of 60 inches, bolt radius of 0.281 inches and having a pre-defined mass density. The data in terms of frequency as a function of tension is as follows:

TABLE 1

| LOAD | \multicolumn{10}{c}{FREQUENCY AS FUNCTION OF TENSION} | | | | | | | | | |
|---|---|---|---|---|---|---|---|---|---|---|
| | N = 1 | N = 2 | N = 3 | N = 4 | N = 5 | N = 6 | N = 7 | N = 8 | N = 9 | N = 10 |
| 0. | 12.4 | 49.6 | 111.7 | 198.5 | 310.2 | 446.7 | 608.0 | 794.2 | 1005.1 | 1240.9 |
| 500. | 18.6 | 56.8 | 119.1 | 206.1 | 317.8 | 454.3 | 615.7 | 801.8 | 1012.8 | 1248.6 |
| 1000. | 23.1 | 63.1 | 126.1 | 213.3 | 325.2 | 461.8 | 623.2 | 809.4 | 1020.4 | 1256.2 |
| 1500. | 26.9 | 68.9 | 132.7 | 220.4 | 332.5 | 469.2 | 630.6 | 816.9 | 1027.9 | 1263.7 |
| 2000. | 30.3 | 74.2 | 139.0 | 227.2 | 339.5 | 476.4 | 638.0 | 824.3 | 1035.4 | 1271.2 |
| 2500. | 33.3 | 79.2 | 145.1 | 233.8 | 346.5 | 483.6 | 645.3 | 831.7 | 1042.8 | 1278.7 |
| 3000. | 36.0 | 83.9 | 150.9 | 240.2 | 353.3 | 490.6 | 652.5 | 839.0 | 1050.2 | 1286.1 |
| 3500. | 38.6 | 88.3 | 156.4 | 246.5 | 360.0 | 497.6 | 659.6 | 846.2 | 1057.5 | 1293.5 |
| 4000. | 41.0 | 92.5 | 161.8 | 252.6 | 366.5 | 504.4 | 666.6 | 853.4 | 1064.8 | 1300.9 |
| 4500. | 43.2 | 96.5 | 167.0 | 258.6 | 373.0 | 511.2 | 673.6 | 860.5 | 1072.0 | 1308.2 |
| 5000. | 45.4 | 100.4 | 172.1 | 264.4 | 379.3 | 517.8 | 680.5 | 867.5 | 1079.2 | 1315.4 |
| 5500. | 47.4 | 104.1 | 177.0 | 270.1 | 385.5 | 524.4 | 687.3 | 874.5 | 1086.3 | 1322.6 |
| 6000. | 49.4 | 107.7 | 181.8 | 275.7 | 391.6 | 530.9 | 694.1 | 881.5 | 1093.4 | 1329.8 |
| 6500. | 51.3 | 111.2 | 186.4 | 281.1 | 397.7 | 537.3 | 700.8 | 888.4 | 1100.4 | 1337.0 |
| 7000. | 53.1 | 114.6 | 191.0 | 286.5 | 403.6 | 543.7 | 707.4 | 895.2 | 1107.4 | 1344.1 |
| 7500. | 54.9 | 117.9 | 195.4 | 201.8 | 409.5 | 549.9 | 713.9 | 902.0 | 1114.3 | 1351.1 |
| 8000. | 56.6 | 121.1 | 198.8 | 207.0 | 415.3 | 556.1 | 720.5 | 908.7 | 1121.2 | 1358.2 |
| 8500. | 58.2 | 124.2 | 204.0 | 302.0 | 420.9 | 562.3 | 726.9 | 915.4 | 1128.1 | 1365.2 |
| 9000. | 59.9 | 127.2 | 206.2 | 307.1 | 426.6 | 568.3 | 733.3 | 922.0 | 1134.9 | 1372.1 |
| 9500. | 61.4 | 130.2 | 212.2 | 312.0 | 432.1 | 574.3 | 739.6 | 928.6 | 1141.7 | 1379.0 |
| 10000. | 63.0 | 133.1 | 216.2 | 316.8 | 437.6 | 580.3 | 745.9 | 935.2 | 1148.4 | 1385.9 |

For a given bolt radius, as the bolt length is increased, the various mode frequencies will be proportionately decreased but still distinctly defined in each case. Practices now establish that reading of the fourth frequency mode, i.e., mode alignment 60 in FIG. 2, may be most reliable due to large amplitude and linear alignment. However, it should be kept in mind that various of the frequency vibration mode alignments will provide the requisite data comparison for roof bolts of differing tensions. In addition, the vibrating natural frequencies appear to be independent of the method of excitation; that is, there was found to be no difference in frequency response between excitation parallel to and perpendicular to the bolt axis.

Mine roof stability monitoring may be carried out through essentially the same apparatus as is illustrated in FIG. 1. That is, the striking instrument 28 is used to excite a portion of the mine roof as at ceiling position 38 and one or more transducers 30 are disposed to detect such excitation at spaced distances along the roof surface 14. It has been found that a weak mine roof will generate sound whose dominant frequencies are less than 500 Hz., and this frequency does not depend upon the amount of input energy.

Figure 3:
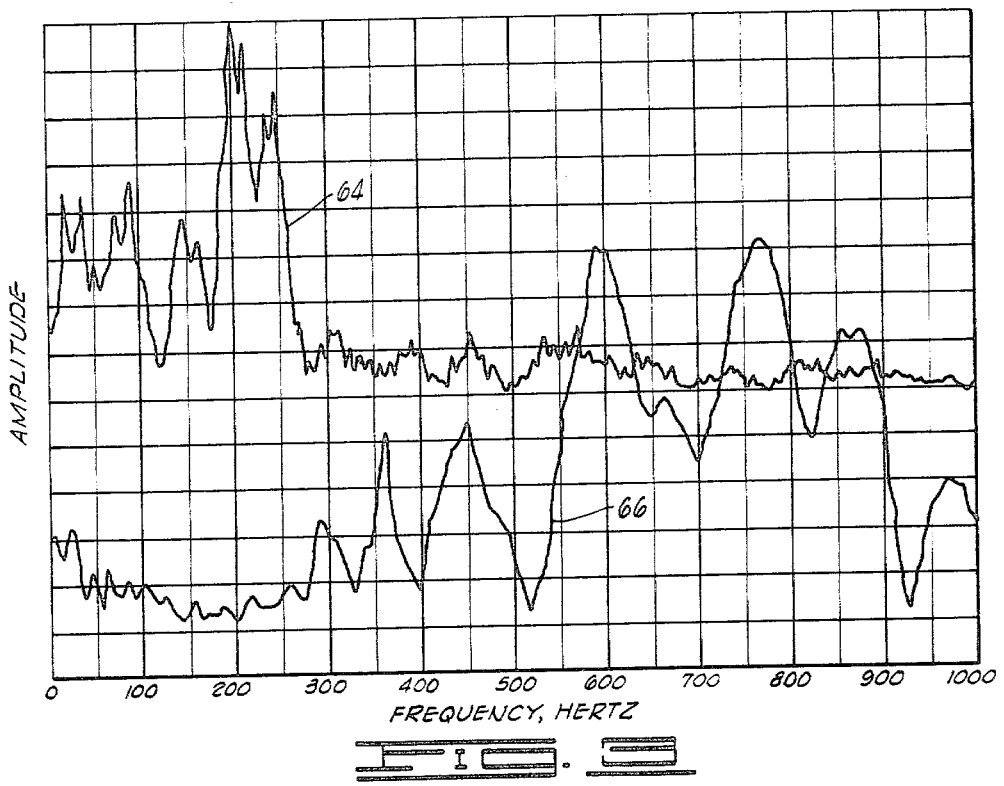
FIG. 3 is a graph of a plurality of strike signals as illustrated in amplitude versus frequency.
Figure 4:
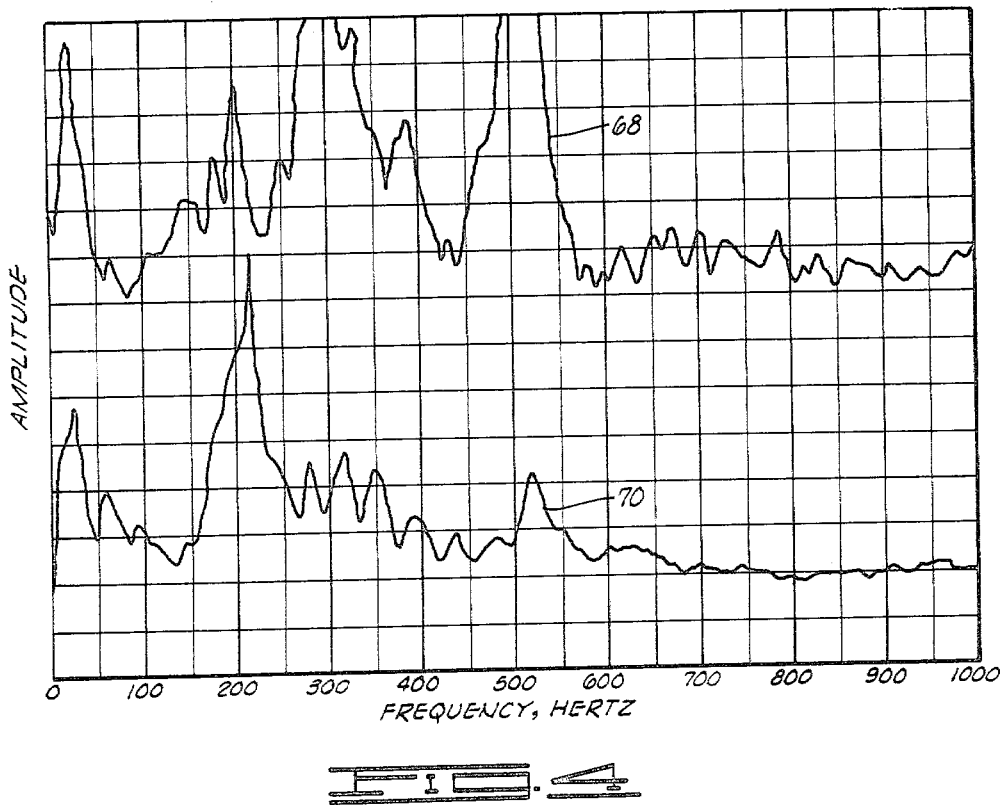
FIG. 4 is a graph of comparative sonic energy pickup devices in amplitude and frequency.
Figure 3:
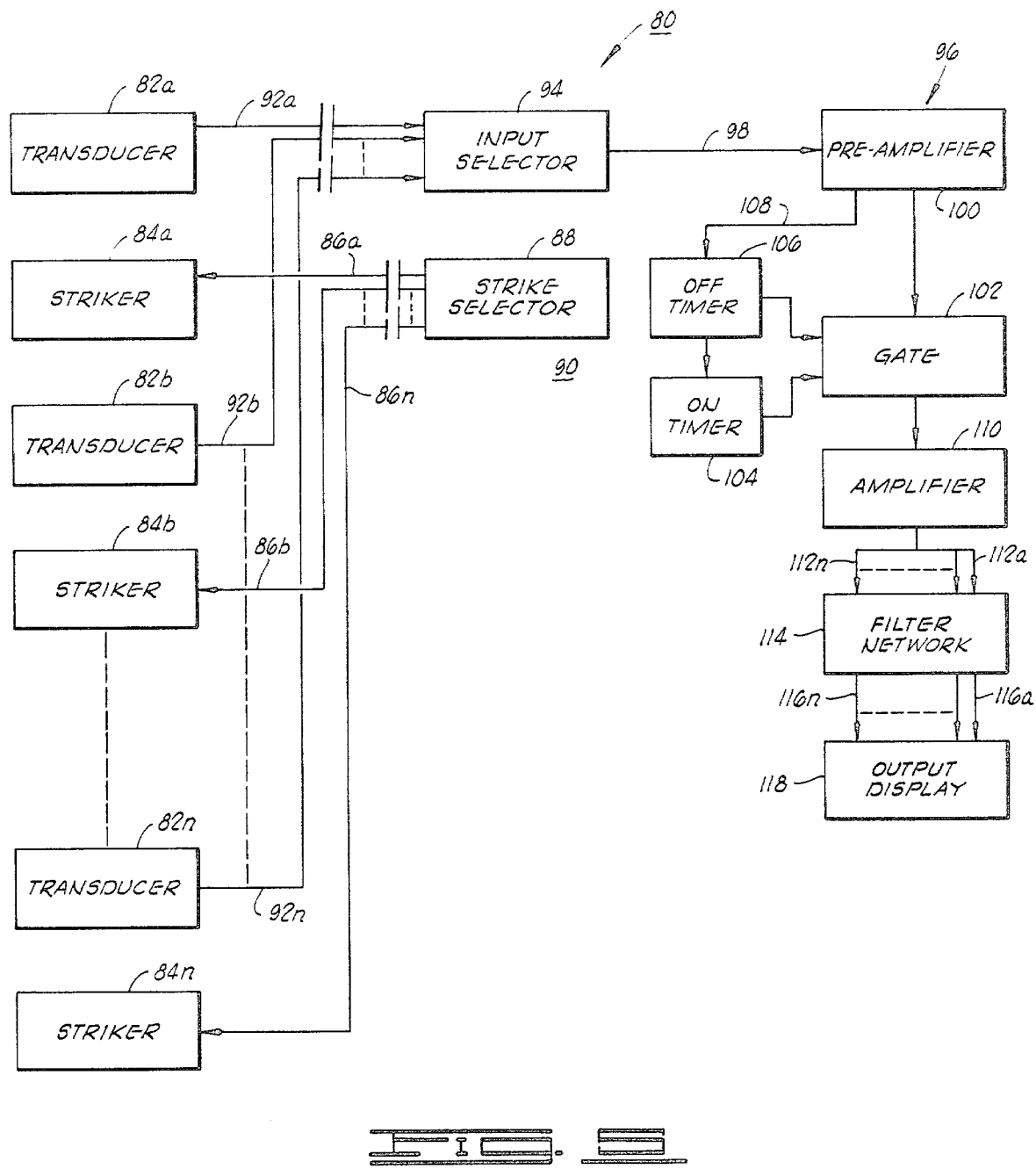

FIG. 3 illustrates response curves for weak and strong mine roofs as detected and analyzed by the same equipment. The upper curve 64 was derived from a weak roof section as is apparent from the predominance of energy indication from 0 to 300 Hz. The lower curve 66 is illustrative of a strong roof response and exhibits a predominance of energy indication in the range of 400–1000 Hz. The particular energy detection for the data of FIG. 3 was derived using both microphone and seismic probe, and it was found that these produced qualitatively similar responses when the distance between transmitters and transducers was relatively close. This is illustrated in FIG. 4, a typical weak roof response, wherein curve 68 illustrates the microphone response, and curve 70 illustrates the seismic probe response. Such similarity of dynamic response may be assumed to be a characteristic of coal mine roof structures.

FIG. 5 illustrates apparatus as it may be installed on a relatively permanent basis at particularly hazardous or critical mine locations with interrogation and data analysis carried out at a central or remote location. Thus, a plurality of transducers 82a-n may be positioned at designated locations for detection of energy in either a roof bolt or a roof surface position. A plurality of strikers 84a-n are then similarly located in proximate relationship to the related transducer 82a-n. Strikers 84 may be such as solenoid-type strikers as electrically actuated via lines 86a-n from a strike selector 88 located at the remote operating position 90. Signals detected by transducers 82a-n are then returned via lines 92a-n to a remote input selector 94 which then applies the signals in designated order or selection to test apparatus 96.

The test apparatus 96 is more particularly described in the related patent application filed concurrently herewith and entitled "Electronic Mine Roof Testing Apparatus" U.S. Ser. No. 37,691, filed May 10, 1979, to Stanley E. Hinshaw and Charles F. Cole, Jr. Selected input from input selector 94 is applied via line 98 to a preamplifier 100 with output applied to a gate circuit 102. Gate 102 is opened and closed by ON timer 104 and OFF timer 106 as controlled by an initiation signal on lead 108 from preamplifier 100. The apparatus 96 is presently constructed of IC circuitry such that the preamplifier 100 may be such as a Type 747 operational amplifier, one or more stages, and the gate 102 may be an analog type NAND gate such as Fairchild Type AH0134CD. The timer circuits 104 and 106 may each consist of a bi-stable timer circuit such as Signetics Type NE555.

Output from gate 102 is then applied to an amplifier circuit 110 which provides a plurality of parallel outputs 112a-n to a comb filter network 114 that provides a plurality of frequency selective throughputs with output on respective leads 116a-n. In present construction, the filter network 114 covers the range of frequencies from 200 Hz. to 400 Hz. and provides ten throughput channels each 20 Hz. wide. Thus, output signal on leads 116a-n may each carry a signal from one of the ten 20 Hz. band filters, and if this signal is present it will energize a respective associated indication at output display 118. Output display 118 may be such as ten separate LED channels which are selectively energized in accordance with comb filter inputs.

The operator can test selected locations by means of strike selector 88 working in conjunction with input selector 94, and as signal is received and input to preamplifier 100 the LED output display 118 will indicate the signal response characteristics by illumination of selected ones of 10 LED'S, each representing a particular 20 Hz. segment between 200 and 400 Hz. The 200-400 Hz. range is selected as being a good indicator range for both roof bolt and roof stability indications as can be seen from FIGS. 2 and 3. However, it should be understood that this range and number of segments is entirely a matter of choice and can be altered in accordance with the exigencies of particular situations.

The foregoing discloses an improved method and apparatus for measuring both roof bolt tension and mine roof stability more accurately and rapidly than has heretofore been achieved. The method enables more regular surveillance of mine roof conditions thereby to improve the overall safety of underground mining operations. The apparatus has the capability of full automation that can enable continuous surveillance as to the condition of mine roof structures, and continual data collection over a period of time can enable indication of any trends or changes in roof structures such that correctional action may be instituted.

Changes may be made in the combination and arrangement of elements as heretofore set forth in the specification and shown in the drawings; it being understood that changes may be made in the embodiments disclosed without departing from the spirit and scope of the invention.

The embodiments of the invention in which an exclusive property or privilege is claimed are defined as follows:

1. A method of testing mine roof stability, comprising the steps of:
    exciting the mine roof bolt to vibration at the natural occurring frequencies by normal tightening of the roof bolt;
    detecting the natural occurring frequency vibrations; and
    analyzing spectrally to determine the predominance of frequency distribution within the range of natural occurring frequencies between zero and 1,000 Hz. to provide an indication of roof bolt tension thereby to derive an indicator of mine roof stability.

* * * * *